(12) United States Patent
Perrotto et al.

(10) Patent No.: US 8,911,790 B2
(45) Date of Patent: *Dec. 16, 2014

(54) SOLID COMPOSITION CONTAINING A HYPOTHIOCYANITE SALT

(71) Applicants: Alaxia SAS, Lyons (FR); Stragen Pharma SA, Plan-les-Ouates (FR)

(72) Inventors: Sandrine Perrotto, Fleurieu sur l'Arbresle (FR); Sébastien Gluszok, Givenchy en Gohelle (FR); Philippe Bordeau, St Pierre de Chandieu (FR); Catherine David, Annecy le Vieux (FR)

(73) Assignees: Alaxia SAS, Lyons (FR); Stragen Pharma SA, Plan-les-Ouates (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/350,446

(22) PCT Filed: Oct. 10, 2012

(86) PCT No.: PCT/EP2012/070092
§ 371 (c)(1),
(2), (4) Date: Apr. 8, 2014

(87) PCT Pub. No.: WO2013/053777
PCT Pub. Date: Apr. 18, 2013

(65) Prior Publication Data
US 2014/0255382 A1   Sep. 11, 2014

Related U.S. Application Data

(60) Provisional application No. 61/545,691, filed on Oct. 11, 2011.

(30) Foreign Application Priority Data

Oct. 10, 2011 (FR) ..................................... 11 59138

(51) Int. Cl.
*A61K 33/00* (2006.01)
*A61K 33/04* (2006.01)
*C12P 3/00* (2006.01)
*A61K 45/06* (2006.01)

(52) U.S. Cl.
CPC . *A61K 33/04* (2013.01); *C12P 3/00* (2013.01); *A61K 45/06* (2013.01)
USPC ........................... 424/611; 424/607; 424/610

(58) Field of Classification Search
None
See application file for complete search history.

(56) References Cited

U.S. PATENT DOCUMENTS

| 8,263,138 | B2 | 9/2012 | Perraudin |
| 2004/0156917 | A1 | 8/2004 | Conner |
| 2006/0018817 | A1 | 1/2006 | Ashby |
| 2009/0246146 | A1 | 10/2009 | Banfi et al. |
| 2009/0317378 | A1 | 12/2009 | Perraudin |
| 2013/0089620 | A1 | 4/2013 | Perrotto et al. |

FOREIGN PATENT DOCUMENTS

| WO | WO-2002/097076 A1 | 12/2002 |
| WO | WO-2007/134180 A2 | 11/2007 |
| WO | WO-2008/003688 A1 | 1/2008 |
| WO | WO-2008/045696 A2 | 4/2008 |
| WO | WO-2010/086530 A1 | 8/2010 |
| WO | WO-2010/086531 A1 | 8/2010 |

OTHER PUBLICATIONS

Singh, A.K., et al. (2009) "Inhibition of lactoperoxidase by its own catalytic product: crystal structure of the hypothiocyanate-inhibited bovine lactoperoxidase at 2.3-Åresolution", *Biophysical Journal*, 96:646-654.

Pollock, J., et al. (1992) "Lactoperoxidase-catalyzed oxidation of thiocyanate ion: a carbon-13 nuclear magnetic resonance study of the oxidation products" *Biochimica et Biophysica Acta*, 1159:279-285.

Written Opinion dated Nov. 19, 2012 issued in PCT Patent Application No. PCT/EP2012/070092 with Full English Translation.

International Search Report and Written Opinion dated Nov. 19, 2012 issued in PCT Application No. PCT/EP2012/070092 with English Translation.

Preliminary International Search Report and Written Opinion dated Mar. 21, 2012 issued in French Application No. 1159138—No English Translation.

*Primary Examiner* — Jeffrey T Palenik
(74) *Attorney, Agent, or Firm* — Harness, Dickey & Pierce, P.L.C.

(57) ABSTRACT

The present invention relates to a solid composition including at least one hypothiocyanite (OSCN⁻) salt combined with a cation, wherein said solid composition is in the form of an amorphous and/or crystalline powder. The invention also relates to a method for producing said solid composition, and to the use thereof.

19 Claims, 6 Drawing Sheets

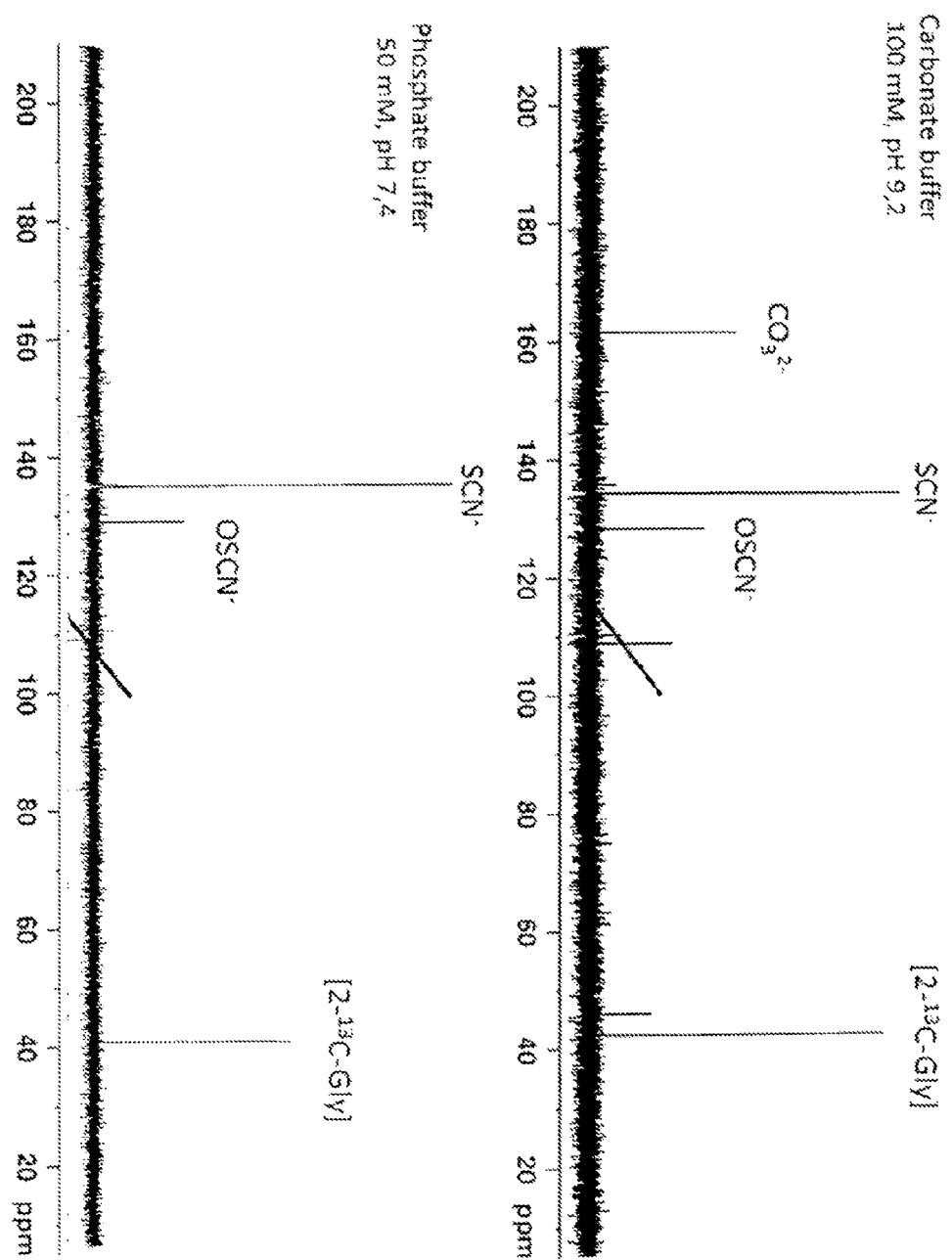
Fig 1.A

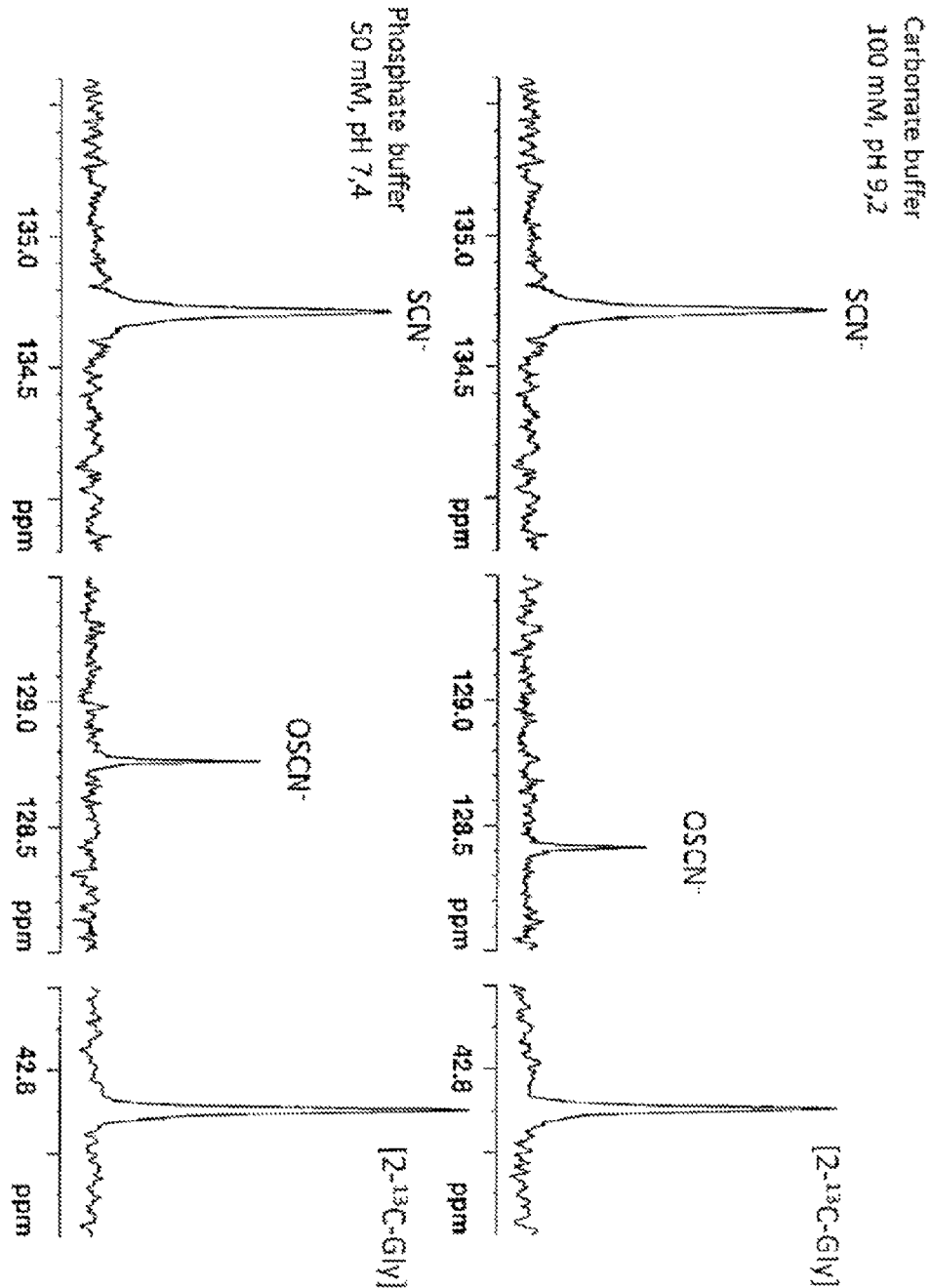
Fig 1.B

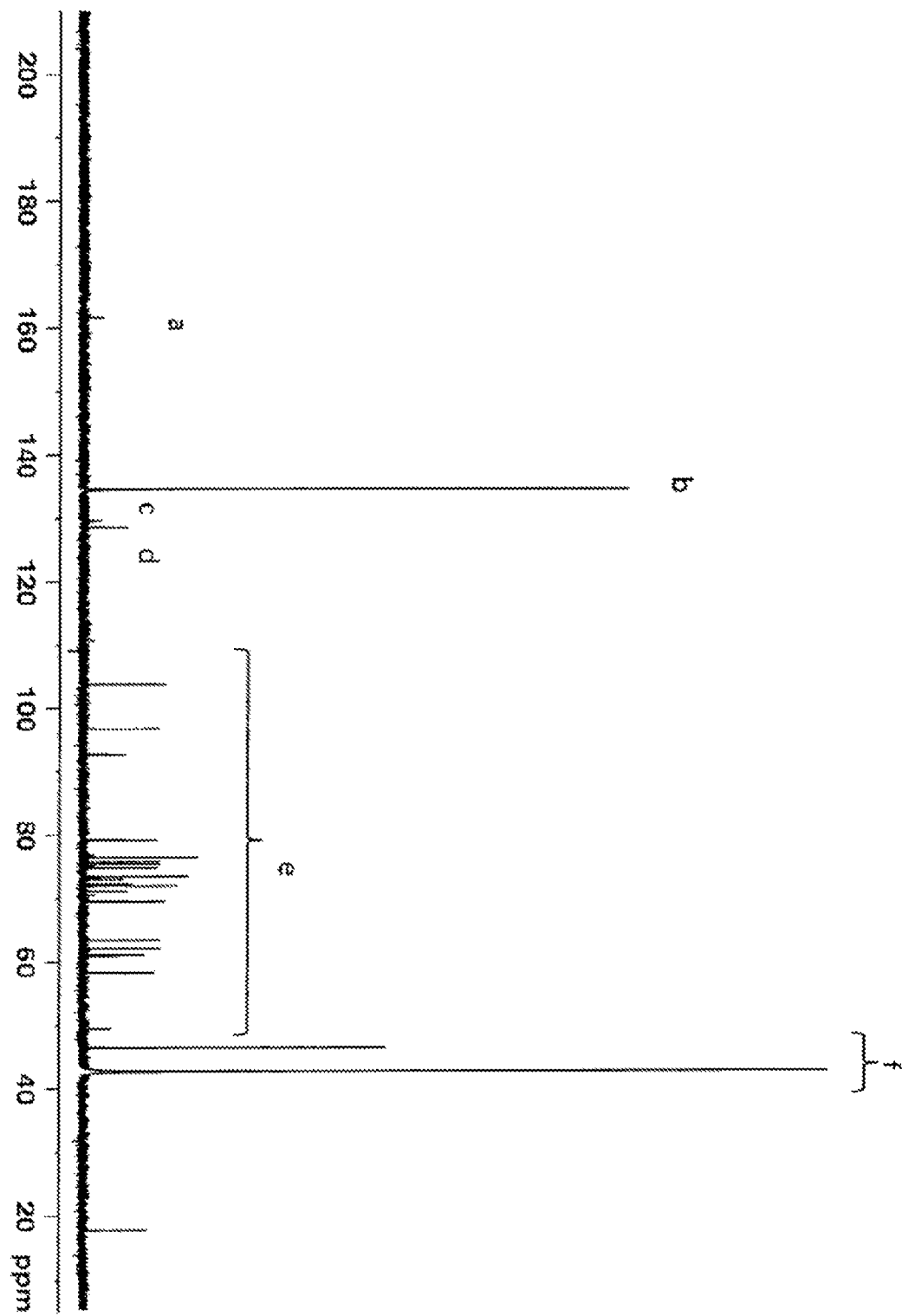

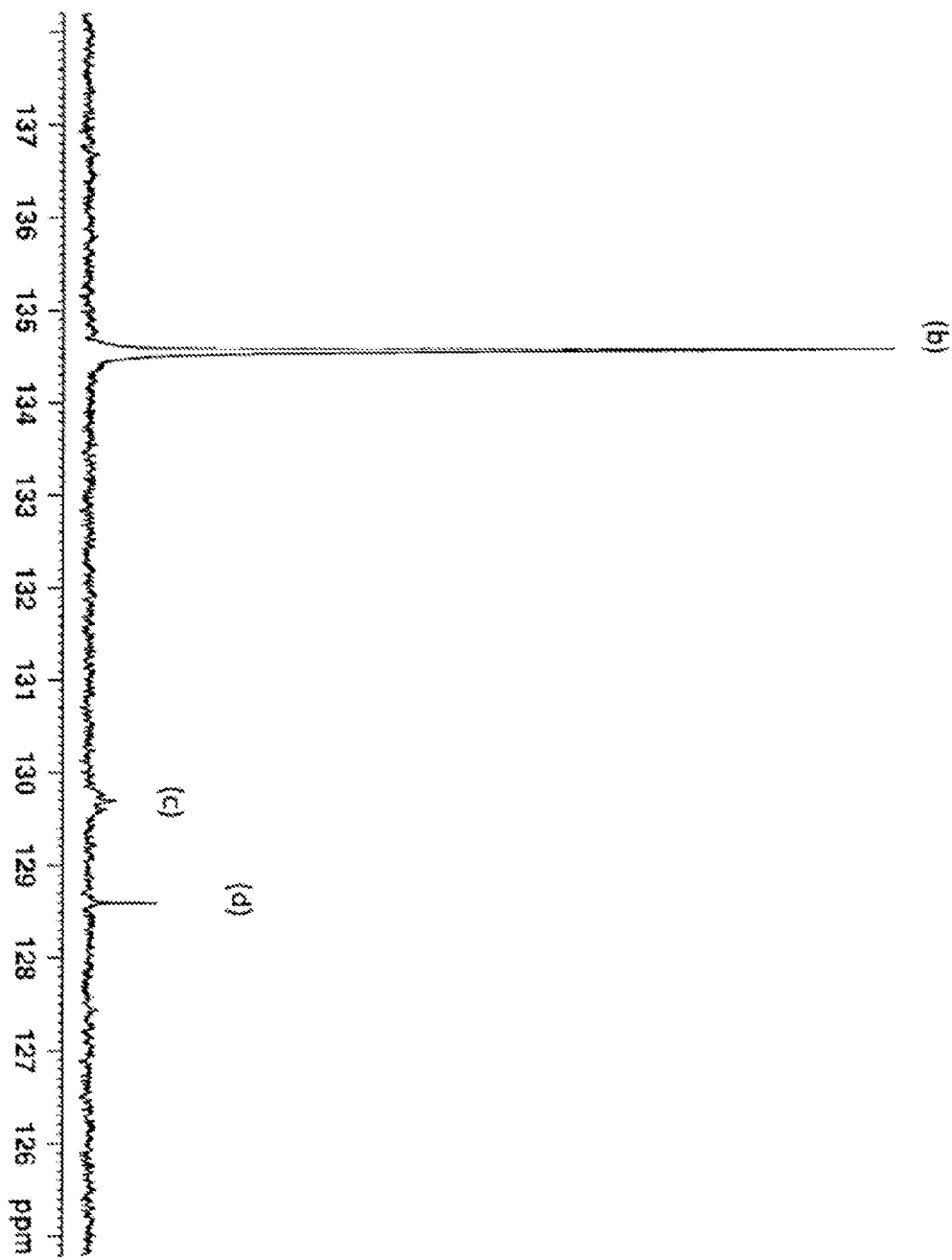
Fig 3.B

SOLID COMPOSITION CONTAINING A HYPOTHIOCYANITE SALT

PRIORITY STATEMENT

This application is a national stage application under 35 §371 of PCT International Application No. PCT/EP2012/070092 which has a International filing date of 10 Oct. 2012, which claims priority under 35 U.S.C. §119 to French Application NO. 1159138 filed 10 Oct. 2011 and United States Provisional Application No. 61/545,691 filed 11 Oct. 2011. The contents of each application recited above are incorporated herein by reference in their entirety.

FIELD OF INVENTION

The purpose of this invention is a solid composition comprising at least an $OSCN^-$ hypothiocyanite salt combined with a cation, with such solid composition having the form of an amorphous and/or crystalline powder. The invention also concerns the manufacturing process of said composition and its use.

CONTEXT OF THE INVENTION

The food and pharmaceutical industry are showing a strong interest in hypothiocyanite as a bactericidal ion.

The hypothiocyanite ion and/or hypohalite is generated among other in vivo in a solution by the lactoperoxidase system according to the following equation:

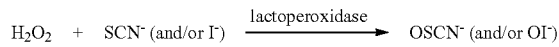

$$H_2O_2 + SCN^- (\text{and/or } I^-) \xrightarrow{\text{lactoperoxidase}} OSCN^- (\text{and/or } OI^-)$$

The pharmacological properties of the hypothiocyanite ion are known, namely, its biocidal properties and in particular the microbiocidal properties, but due to the instability of this chemical species of which the half-life is less than 24 hours, uses are delicate, complicated and limited and its storage for extended periods of time is not possible ("Mechanism of Decomposition of the Human Defense Factor Hypothiocyanite Near Physiological pH", Jozsef Kalmar, Kelemu L. Woldegiorgis, Bernadett Biri, and Michael Thomas Ashby; *J. Am. Chem. Soc.*, 2011, 133 (49), pp 19911-19921).

Due to this instability, the lactoperoxidase system was initially often delivered complete in the form of a powder that enabled generating the $OSCN^-$ ion in situ by triggering the reaction, for instance by placing the reaction components in a solution. According to the uses, the oxygen donor could be a hydrogen peroxide, a sodium percarbonate or be generated in situ by the glucose/glucose oxidase system.

The lactoperoxidase system is used for instance in cosmetic products such as toothpastes marketed by the Laclede company under the Biotene® name. More recently, one has observed the appearance of patent applications for the use of the lactoperoxidase system in human health. For instance, application WO2008/045696 deals with a method of usage of these compounds for the treatment of vaginal disorders. Once can also mention methods and compositions to treat pulmonary problems (US 2004/0156917 and WO2007/134180).

Variants with possible substitution of the thiocyanate pseudohalogen by iodine (US 2009/0246146) in combination or not with a peroxidase have also been proposed. All applications described used, either the production in situ by administration of the complete system, and/or a part of the system with use of one of the endogenous components present in situ.

A step has been cleared by proposing a process permitting the production of $OSCN^-$ and/or $OI^-$ agents with separation of the enzyme precursors through the use of coagulant agents (WO2002/097076) which led to the production of $OSCN^-$ and/or $OI^-$ in a large volume solution. In fact, WO2010/086530 describes materials which enable to produce, extemporaneously, as needed, a solution comprising $OSCN^-$ or $OI^-$.

POLLOCK J R et al: "lactoperoxidase-catalyzed oxidation of thiocyanate ion: a carbon-13 nuclear magnetic resonance study of the oxidation products", BIOCHEMICA ET BIOPHYSICAL ACTA. PROTEIN STRUCTURE AND MOLECULAR ENZYMOLOGY, ELSEVIER, vol. 1159, No.-3, 20 Oct. 1992, pages 279-285, XP023469659, SSN: 0167-4838, reveals the preparation of a solution comprising a hypothiocyanite ion from thiocyanate and $H_2O_2$ catalyzed by lactoperoxidase. The object of this invention differs from the prior state of the art in that the composition of the invention containing the hypothiocyanite ion is solid. In fact, the problem that this invention intends to resolve can be considered as the preparation of a composition comprising a hypothiocyanite salt that can be stored over a long period of time. None of the documents of the prior state of the art mentions a solid composition comprising a hypothiocyanite salt. US 2006/018817A1 (ASHBY MICHAEL) proposes the preparation of a hypothiocyanite ion from thiocyanate and hypochlorous acid in which the composition is liquid. WO 2010/086530 A1 (ALAXIA) describes a composition comprising hypothiocyanite ions and lactoferrin administered by a sprayer, nebulizer or aerosol. However, there is no solid composition comprising a hypothiocyanite salt that can be stored for a long period of time.

As such, one of the major problems of using this active agent is its instability and as a result, the impossibility of storing it over a long period of time in accordance with the requirements of the pharmaceutical regulations leading to its extemporaneous production.

SUMMARY OF THE INVENTION

The invention involves a solid composition comprising at least an $OSCN^-$ hypothiocyanite salt combined with a cation in the form of an amorphous and/or crystalline powder.

The invention also involves a manufacturing process of said solid composition with this process comprising the following steps:

a) Prepare an aqueous solution containing at least the $OSCN^-$ hypothiocyanite ion;
b) Add to said aqueous solution, at least an alcohol or an organic solvent take from among the azeotropes of water, at a percentage between 10 and 99.9%;
c) Add to said solution an excipient of the osidic, polyosidic or polyol type.
d) Eliminate said alcohol or the organic solvent at a pressure between 1 mbar and 80 bars and a temperature between −100° C. and +50° C. in order to obtain a solid composition.

The invention is also aimed at using said composition alone or in combination with other microbiocidal, antimicrobial, antiviral, preservatives or antibiotic agents for treating airborne infections, the lower respiratory tracts and/or the upper respiratory tracts.

Another purpose of the invention is the use of said solid composition alone or in combination with other microbiocidal, antimicrobial, antiviral, fungicidal, preservative or antibiotic agents for treating selected infections among the group comprising gastric, cut, mucosa membranes and/or skin infections.

The invention also involves the use of said composition alone or in combination with other antimicrobial, antiviral, antiparasitic, fungicide, preservative or antibiotic agents for treating bacteria, yeasts, molds, virus, prions, parasites, protozoan species.

In addition, the invention also involves the use of said composition, alone or in combination with other agents for treating influence type viral infections.

Another purpose of the invention involves the use of said composition, alone or in combination with other compounds as a component to improve the mucociliary clearance.

Other objects and benefits of this invention will appear upon reading the description and the embodiment examples.

BRIEF DESCRIPTION OF THE FIGURES

FIGS. 1A and 1B: Showing the RMN$^{13}$C spectrum of gross filtrates obtained for two different buffers (carbonate buffer or phosphate buffer) before adding lactose and evaporation. (Example 7). FIG. 1A represents the complete spectrum and FIG. 1B the expansion of the window containing the hypothiocyanite signal.

FIGS. 3A and 3B. Representation of the RMN$^{13}$C spectrum of solid composition No. 2 (example 12). FIG. 3A represents the complete spectrum and FIG. 3B an enlargement of the window containing the hypothiocyanite signal.

DETAILED DESCRIPTION OF THE INVENTION

Figure 2:
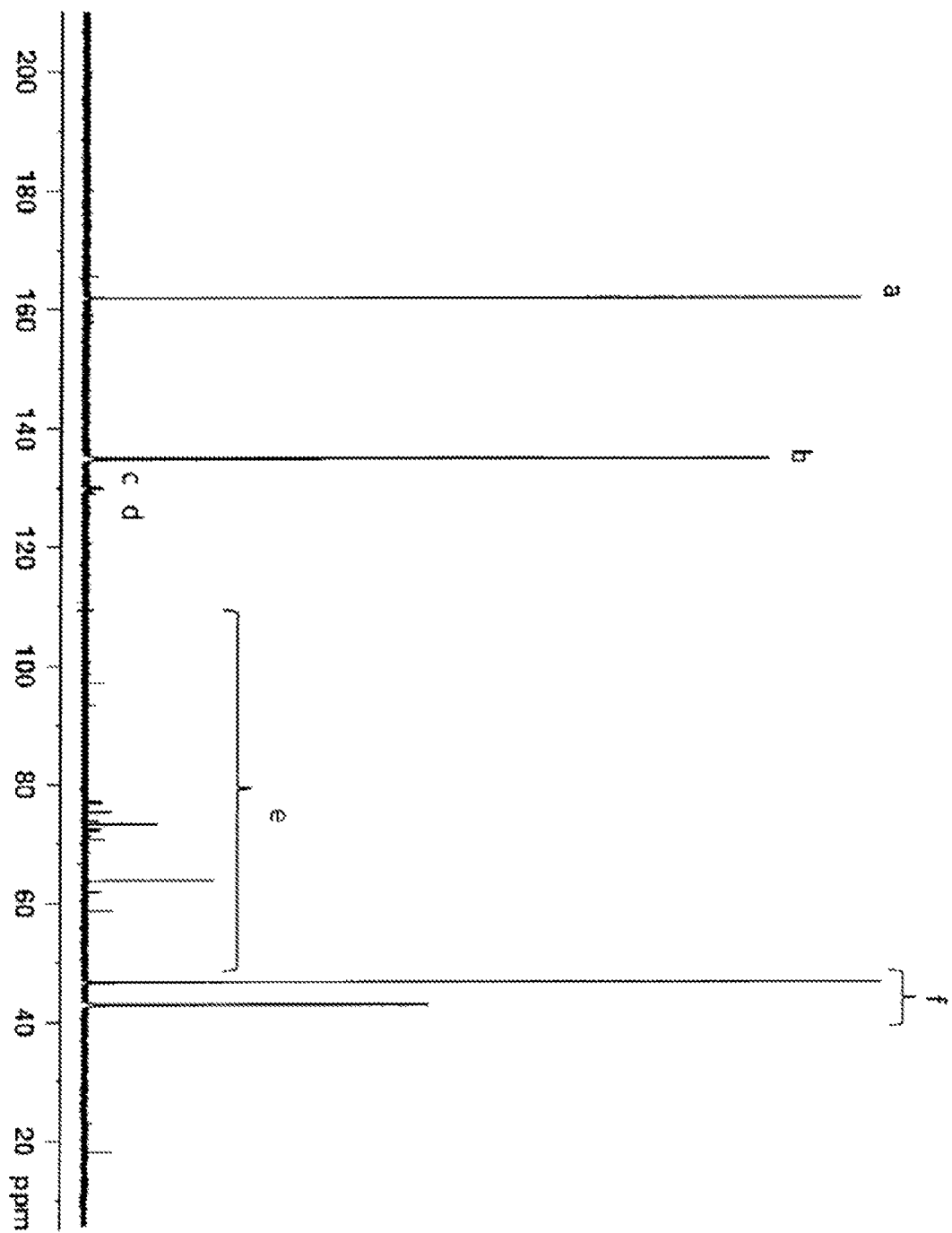
FIG. 2: Representation of the RMN$^{13}$C spectrum of solid composition No. 1 (example 11).

This invention permits obtaining a composition that comprises at least a hypothiocyanite salt OSCN$^-$ combined with a cation in a solid form, with said solid composition having the form of an amorphous and/or crystalline powder.

This invention also concerns a solid composition characterized in that it contains at least an hypothiocyanite salt OSCN$^-$ combined with a cation, in the form of an amorphous and/or crystalline powder in a percentage by weight ranging between 0.01% and 20% and preferably between 0.01% and 10%.

According to a method of embodiment, the composition according to the invention is characterized in that it also contains a thiocyanate ion salt (SCN$^-$) in a percentage by weight ranging between 0.01% and 40% and preferably between 0.01% and 10%.

According to another method of embodiment, the composition according to the invention also comprises gluconic acid in a percentage by weight between 0.01% and 20%.

According to an additional method of embodiment, the composition according to the invention also comprises a phosphate or carbonate salt combined with an alkaline cation in a percentage by weight ranging between 10 and 99.999%.

According to a preferred method of embodiment, the cation according to the invention is selected among alkaline cations like sodium, and potassium or in the group made up of calcium and/or magnesium.

According to another method of embodiment, the solid composition according to the invention comprises an excipient of the osidic, polyosidic or polyol type, and preferably said solid composition comprises a combination of at least two of said osidic, polyosidic and polyol excipients.

Said excipients are for instance beneficially selected among glucose, lactose, trehalose, mannitol and/or their mixtures.

According to a method of embodiment, the composition contains mannitol at a percentage by weight between 1 and 50%.

According to another method of embodiment, the composition according to the invention is characterized in that trehalose is present at a percentage by weight between 1 and 45%.

According to a special method of embodiment, the solid composition according to the invention contains lactose present at a percentage by weight between 1 and 60%.

In the composition according to the invention, hypothiocyanite ion OSCN$^-$ is stable over a minimum period of 2 months and up to 6 months.

Preferably, hypothiocyanite ion OSCN$^-$ is stable over a minimum period of 2 months and up to 4 months.

The composition according to the invention will preferably be kept at a temperature between +20° C. and −80° C., protected against oxygen, moisture and light.

An important benefit of the solid composition according to the invention resides in the fact that now it is possible to increase the concentration of OSCN$^-$ hypothiocyanite in the reconstituted solution ready for use that will be administered to the patient. As such, it is possible to have a greater OSCN$^-$ hypothiocyanite dose and as such, inject patients with lower volumes of product, which is quicker, more beneficial and less painful for the patient.

In addition, the invention concerns a solution ready for use characterized in that it comprises a solid composition according to the invention, solubilized in an acceptable environment at a physiological level. For example, the solid composition will be solubilized in an acceptable organic solvent selected among hydroalcoholic solvents or among compounds carrying hydroxyl functions or any other physiologically acceptable solvent know to the expert in the field.

Preferably, the hydroalcoholic solvent comprises an alcohol representing between 0.01% and 100% by weight of said solvent.

The invention also concerns a manufacturing process of said solid composition comprising the following steps:
  a) Prepare an aqueous solution containing at least the OSCN$^-$ hypothiocyanite ion;
  b) Add to said aqueous solution, at least an alcohol or an organic solvent taken from among the azeotropes of water, at a percentage between 10 and 99.9%;
  c) Add to said solution an osidic, polyosidici or polyol type excipient;
  d) Eliminate said alcohol or organic solvent at a pressure between 1 mbar and 80 bars and a temperature between −100° C. and +50° C. in order to obtain a solid composition.

According to a method of embodiment, the process according to the invention is characterized in that the organic solvent is selected among the classically described azeotropes of water, as well as their combination.

An azeotrope or azeotropic mixture is a liquid mixture that boils at a fixed temperature while keeping a fixed composition. An azeotropic mixture is a mixture that presents for a given composition, a vapor phase having the same composition as the liquid phase with which it is in balance.

According to a method of embodiment, the process according to the invention is characterized in that said alcohol is selected among ethanol, propanol, isopropanol, tert-butanol or their mixtures.

According to a method of embodiment, the process according to the invention is characterized in that a combination of at least two of said alcohols is added to the aqueous solution.

According to a special method of embodiment, the alcohol or organic solvent proportions may vary between 1 and 99% with respect to the aqueous solution containing the OSCN⁻.

According to a preferred method of embodiment, the process according to the invention is characterized in that the alcohol is ethanol at a percentage between 1% and 99%.

According to a method of embodiment, the excipient is of the osidic, polyosidic or polyol type. Preferably, the excipient is selected among the group of mannitol, trehalose, lactose, glycerol of PEG (polyethylene glycol) and/or their mixtures.

According to a special method of embodiment, the process according to the invention is characterized in that the polyol type excipient is glycerol at a percentage by weight between 10 and 50%.

According to another method of embodiment, the process according to the invention is characterized in that the polyol type excipient is polyethylene glycol (PEG) at a percentage by weight between 10 and 50%.

According to a method of embodiment, the process according to the invention is characterized in that the polyol type excipient is mannitol at a percentage by weight between 1 and 50%.

According to a method of embodiment, the process according to the invention is characterized in that the polyosidic type excipient is trehalose at a percentage by weight between 1 and 45%.

According to another method of embodiment, the process according to the invention is characterized in that the polyosidic type excipient is lactose at a percentage by weight between 1 and 60%.

According to a method of embodiment, the process according to the invention is characterized in that the temperature at step d) is set between 0° C. and −100° C. Preferably, the temperature is set between −10° C. and 80° C. According to another preferred method of embodiment, the temperature is set at −20° C. According to a special method of embodiment, the temperature is set at −80° C.

According to a method of embodiment, the process according to the invention is characterized in that the solvents are removed simultaneously.

According to another method of embodiment, the process according to the invention is characterized in that said alcohol or organic solvent is removed consecutively.

According to a mode of embodiment of the invention, water is removed first.

According to another method of embodiment, said alcohol or the organic solvent is removed by evaporation in the form of an azeotrope, at reduced pressure. Preferably, evaporation is achieved at a temperature between 20 and 45° C.

According to a mode of embodiment, the process according to the invention is characterized in that the evaporation is achieved at ambient temperature. According to a special method of embodiment, the process according to the invention is characterized in that the evaporation is achieved at low temperature, for instance at a temperature below −80° C. Preferably, evaporation is achieved at reduced pressure.

According to another method of embodiment, said alcohol or the organic solvent is removed by sublimation at low temperature and reduced pressure.

According to a method of embodiment, the process according to the invention is characterized in that said alcohol or organic solvent is removed by lyophilisation.

According to a special method of embodiment, said alcohol or organic solvent is removed by exclusion by using fluids in their super critical or sub critical states used as anti-solvents. According to a method of embodiment according to the invention, one uses for instance the super critical form of $CO_2$.

According to a method of embodiment, the process according to the invention is characterized in that the solvents are removed at pressure/temperature pairs that permit obtaining the super critical or sub critical status.

According to a method of embodiment, the process according to the invention is characterized in that the super critical or sub critical fluids are used as GAS (Gas anti solvent).

According to another method of embodiment, the process according to the invention is characterized in that the super critical or sub critical fluids are used as SAS (Super critical anti solvent).

According to a special method of embodiment, the process according to invention is characterized in that the super critical or sub critical fluids are used as SEDS (Solution Enhanced Dispersion by supercritical fluids).

According to a method of embodiment, the process according to the invention is characterized in that said alcohol or organic solvent is removed at a temperature between 4° C. and 50° C.

According to a method of embodiment, step a) comprises the preparation of the aqueous solution containing the OSCN⁻ hypothiocyanite ion by contact with peroxidase, a halogen and/or a pseudohalogen, and/or an oxygen donor.

According to this method of embodiment, the peroxidase is lactoperoxidase, the pseudohalogen is thiocyanate ion (SNC⁻). According to this mode of embodiment, the hydrogen peroxide is generated in situ by the glucose/glucose oxidase pair.

According to a method of embodiment, the oxygen donor is selected in the group made up of hydrogen peroxide or sodium percarbonate.

According to a method of embodiment, the aqueous solution is buffered and the pH falls within the [6; 11] range. According to this mode of embodiment, the aqueous solution is buffered by a phosphate buffer for which the concentration falls between 50 mM and 200 mM.

According to another method of embodiment, the aqueous solution is buffered by a carbonate buffer for which the concentration falls between 50 mM and 1 M.

According to the invention, the aqueous solution is obtained by enzymatic production according to the successive enzymatic reactions below:

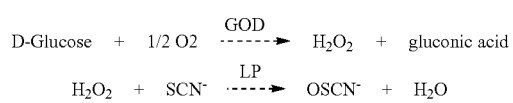

where GOD is glucose oxidase; $H_2O_2$, hydrogen peroxide; LP the lactoperoxidase; SCN⁻ the thiocyanate ion and OSCN⁻ the hypothiocyanite ion.

According to a method of embodiment, the process also comprises between steps a) and b) a filtration stage over a membrane for which the cutting threshold is less than or equal to ≤30 kDa which permits to retain the enzymes.

According to a method of embodiment, said membrane is a membrane for which the cutting threshold is 10 kDa. Preferably, the membrane has a cutting threshold of 5 kDa.

According to a method of embodiment, the process according to the invention is characterized in that the aqueous solution available is available (at step b) also contains carbohydrates such as glucose, gluconic acid, carbonates or their mixtures.

According to a method of embodiment, the process according to the invention is characterized in that the aqueous solution available, also contains the thiocyanate ion.

According to a method of embodiment, the process according to the invention is characterized in that the aqueous solution available is buffered. Preferably, the pH of the aqueous solution of which one disposes falls within the [6; 11] range.

According to a preferred method of embodiment, the aqueous solution available is buffered by a phosphate buffer between 50 mM and 200 mM. Preferably, the aqueous solution available is buffered by a carbonate buffer between 50 mM and 1 M. According to a method of embodiment, the process according to the invention is characterized in that the $OSCN^-$ ion is obtained at a temperature between 0° C. and 40° C.

According to a method of embodiment, the process according to the invention is characterized in that the $OSCN^-$ ion of said aqueous solution is obtained by electrolysis.

According to a method of embodiment, the $OSCN^-$ ion of said aqueous solution is obtained by chemical synthesis.

According to a method of embodiment, the process according to the invention is characterized in that the composition in solid form obtained at step d) is a powder.

According to a method of embodiment, the powder obtained is amorphous.

According to a method of embodiment, the powder obtained is partially crystalline.

According to a method of embodiment, the powder obtained is crystalline.

The invention also concerns the use of the solid composition according to the invention, alone or in combination with other anti-infectious, antimicrobial, antiviral, antifungal or antibiotic agents, or as preservers for treating airborne, lower respiratory tract and/or upper respiratory tract infections.

In particular, the invention concerns also the use of said solid composition, alone or in combination with other anti-infectious, antimicrobial, antiviral, antifungal or antibiotic agents, or as preservers for treating infections combined with cystic fibrosis, the COPD (Chronic Obstructive Pulmonary Disease) and any pathology of the airways. Preferably, the solid composition according to the invention will be used alone or in combination with other active agents as a compound to improve the mucociliary clearance. The mucociliary clearance is an innate critical defense mechanism of the airways made up of a coordinated epithelial transport assembly of water and ions, nucin secretion, ciliary function and cough. The failure of the mucociliary clearance leads to the obstruction and predisposes for chronic bacterial infection.

The invention also concerns the use of said solid composition of the invention, alone or in combination with other anti-infectious, antimicrobial, antiviral, antibiotic, antifungal agents or preservatives for treating infections such as but not exclusively gastric infections, cuts, mucous membranes and/or of the skin.

Another purpose of the invention resides in the use of the solid composition alone or in combination with other anti-infectious, antimicrobial, antiviral, antibiotic, antifungal agents or preservatives for treating infections caused by bacteria and/or yeasts and/or molds and/or viruses and/or prions and/or parasites and/or protozoans. In particular, there is the treatment of viral infections caused by viruses such as the influenza virus. In addition, the solid composition according to the invention is beneficially used alone or in combination for the treatment of the influenza viruses. The solid composition or its reconstituted solution is used among other as treatment in sensitive areas for instance by vaporization or application of said areas.

The solid composition is beneficially combined with proteins or peptides having an antimicrobial activity. The proteins or the peptides of interest having an antimicrobial activity that are combined with the solid composition according to the invention are for instance selected among lactoferrin, lactoferricin and/or lysozyme.

The invention also concerns the use of said solid composition, alone or in combination with other anti-infectious, antimicrobial, antiviral, antibiotic, antifungal agents, or preservatives for direct use of the powder or resolubilisation of the latter in an acceptable physiological environment.

Another purpose of the invention also concerns the use of the solid composition, alone or in combination with other anti-infectious, antimicrobial, antiviral, antibiotic, antifungal agents, or preservatives for the treatment and/or disinfection, sanitization of care materials and medical devices.

The solid composition according to the invention, alone or in combination with other anti-infectious, antimicrobial, antiviral, antibiotic, antifungal agents, or preservatives is aimed to be administered for inhalation, by mouth, topically or by injection.

The invention also concerns the use of the composition according to the invention, alone or in combination with other anti-infectious, antimicrobial, antiviral, antibiotic, antifungal agents, or preservatives for air treatment, by decontamination of the air (passive), ambient decontamination (active) and environmental cleanup.

The invention also concern the use of the solid composition of the invention, alone or in combination with other anti-infectious, antimicrobial, antiviral, antibiotic, antifungal agents, or preservatives for the treatment of foods or drinking water, recreational water and water used for subsequent antimicrobial applications.

The invention also concerns the use of said solid composition, alone or in combination with other, alone or in combination with other anti-infectious, antimicrobial, antiviral, antibiotic, antifungal agents, or preservatives for the stabilization and/or preservation of cosmetics.

The invention also concerns the use of said solid composition alone or in combination with other, alone or in combination with other anti-infectious, antimicrobial, antiviral, antibiotic, antifungal agents, or preservatives for the treatment and/or sanitization of materials and equipment.

The invention also concerns the use of the solid composition, alone or in combination with other anti-infectious, antimicrobial, antiviral, antibiotic, antifungal agents, or preservatives for the treatment of packaging.

Another purpose of the invention concerns the use of said solid composition, alone or in combination with other anti-infectious, antimicrobial, antiviral, antibiotic, antifungal agents, or preservatives for the treatment of textiles.

The invention also concerns the use of said composition, alone or in combination with other anti-infectious, antimicrobial, antiviral, antibiotic, antifungal agents, or preservatives for the treatment of plants.

The invention also concerns the use of said composition, alone or in combination with other anti-infectious, antimicrobial, antiviral, antibiotic, antifungal agents, or preservatives for the treatment of soils.

The invention also concerns the use of said composition, alone or in combination with other anti-infectious, antimicrobial, antiviral, antibiotic, antifungal agents, or preservatives for its co-use with cleaning or disinfection agents.

Another purpose of the invention concerns the use of said composition, alone or in combination with other anti-infectious, antimicrobial, antiviral, antibiotic, antifungal agents, or preservatives for the removal of bacteria, yeasts, molds, viruses, parasites, protozoans.

The solid composition according to the invention is preferably used an antimicrobial, antiviral or anti-parasite agent and aimed for administration by inhalation, by mouth, by topical application or by injection.

The solid composition according to the invention is also usable for the elaboration of a sustained release formulation.

According to a method of embodiment, said sustained release solid composition is preferably encapsulated in combination with other antimicrobial agents, for the treatment of infections selected in a non-limiting manner among the infections of the mucous membranes and/or the skin, as well as respiratory, oral, gastric, intestinal, vaginal infections, cuts and burns.

According to another method of embodiment, said sustained release solid composition is preferably encapsulated in combination with other antiviral, and/or antifungal and/or anti-parasite agents, for the treatment of infections selected in a non-limiting fashion among infections or affections of the mucous membranes, the skin and superficial body growths.

The invention is described in greater detail by the following examples. Other aspects and benefits of this invention will appear when reading the examples which must be considered as illustrative and non-limiting in nature.

EXAMPLES

Example 1

OSCN⁻ Enzyme Production According to Two Successive Enzyme Reactions

Enzyme production following the two successive enzyme reactions below:

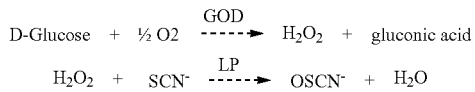

With GOD: Glucose Oxidase; H2O2: Hydrogen peroxide; LP: Lactoperoxidase; SCN-: Thiocyanate; OSCN-: hypothiocyanite ion To a solution of water (100 ml), a 50 mM carbonate buffer and containing 0.4 g of D-glucose and 0.04 g of GOD, 0.12 g of LP are added 1 ml of a 2 M sodium thiocyanate solution (NaSCN). The solution is stirred at ambient temperature at 200 rpm for 10 minutes. The pH of the solution is 9.2.

After reaction, the solution is filtered over a 10 kDa ultra-filtration membrane. A solution is obtained containing:

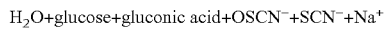

The OSCN⁻ concentration obtained is 1340 μM

Example 2

OSCN⁻ in a Hydroalcoholic Solution

To a diluted solution obtained according to example 1, with an OSCN⁻ concentration of 520 μM are added 20% by weight of absolute ethanol. The temperature is then lowered to −30° C. The solution freezes. An OSCN- ion concentration of 510 μM is measured after a period of 1 month as well as 495 μM after a period of 2 months. The difference observed is due to the precision of the measuring method (spectrophotometry).

Example 3

OSCN⁻ in a Hydroalcoholic Solution

To a diluted solution obtained according to example 1, with an OSCN− concentration of 450 μM, 20% by weight of absolute ethanol is added. The temperature is lowered to −30° C. The solution freezes. An OSCN- ion concentration of 470 μM is measured after a period of 1 month as well as 440 μM after a period of 2 months. The difference observed is due to the precision of the measuring method (spectrophotometry).

Example 4

OSCN⁻ in a Hydroalcoholic Solution

To a diluted solution obtained according to example 1, with an OSCN⁻ concentration of 510 μM, 50% by weight of absolute ethanol is added. The temperature is lowered to −30° C. The solution freezes. An OSCN⁻ ion concentration of 530 μM is measured after a period of 1 month as well as 490 μM after a period of 2 months. The difference observed is due to the precision of the measuring method (spectrophotometry).

Example 5

OSCN⁻ in a Hydroalcoholic Solution

The same solution used according to example 4, with an OSCN− concentration of 510 μM, is preserved at a temperature of −80° C. The solution freezes. An OSCN- ion concentration of 480 μM is measured after a period of 1 month as well as 500 μM after a period of 2 months. The difference observed is due to the precision of the measuring method (spectrophotometry).

Example 6

OSCN⁻ in a Hydroalcoholic Solution

The same solution used according to example 4, with an OSCN⁻ concentration of 510 μM, is preserved at a temperature of −80° C. The solution freezes. An OSCN⁻ ion concentration of 520 μM is measured after a period of 1 month as well as 490 μM after a period of 2 months. The difference observed is due to the precision of the measuring method (spectrophotometry).

The results observed in examples 2 to 7 are assembled in table 1:

TABLE 1

| | OSCN⁻ in a hydroalcoholic solution | | | | |
| --- | --- | --- | --- | --- | --- |
| Example number | Quantity of alcohol in % by weight | Conservation temperature | [OSCN⁻] at T = 0 in μM | [OSCN⁻] at T = 1 month μM | [OSCN⁻] at T = 2 months in μM |
| Example 2 | 20 | −30° C. | 520 | 510 | 495 |
| Example 3 | 20 | −30° C. | 450 | 470 | 440 |
| Example 4 | 50 | −30° C. | 510 | 530 | 490 |
| Example 5 | 50 | −80° C. | 510 | 480 | 500 |
| Example 6 | 50 | −80° C. | 510 | 520 | 490 |

Example 7

RMN of the Two OSCN⁻ Solutions Obtained in Two Different Buffers (Carbonate pH 9.2 and Phosphate pH 7.4). (FIGS. 1A and 1B)

The solutions were obtained according to example 1 with phosphate buffer (100 mM, pH 8), or carbonate (100 mM, pH 9.2). To 0.5 mL of filtered solution, 0.5 mL of $D_2O$ and 20 μl of [2-$^{13}C$]-Gly is added, used as external reference.

FIGS. 1A and 1B illustrate the spectrum $^{13}C$ RMN of the raw filtrate containing the OSCN⁻ recorded for two different buffer conditions (carbonate, pH 9.2 and phosphate, pH 7.4) before the addition of lactose and dry evaporation. Each sample is prepared from 0.5 mL of filtrate, 0.2 mL of $D_2O$ and 20 ul of [2-$^{13}C$]-Gly (0.1 M). The NaS$^{13}$CN (Sigma-Aldrich) has been used as substrate. In both cases, the sample has been analysed within 15 minutes of the synthesis. The spectrum is calibrated according to the [2-$^{13}C$]-Gly used as external reference (the splitting in two of the signal in the carbonate buffer is due to the pH effect). The spectrums have been recorded for 3 hours by a Bruker AM-500 WB type device with a spectral window of 25000 Hz.

Example 8

Solid OSCN⁻ Sodium Salt Obtained by Lyophylization

To a diluted solution obtained according to example 1, with an OSCN⁻ concentration of 450 μM is added 20% of absolute ethanol by weight. The temperature is then lowered to −30° C. The frozen hydroalcoholic solution of example 3 is lyophilized at a pressure between 1 and 10 mbar for 24 hours. A yield of 0.1% or 0.4 μg of Na OSCN⁻ salt is obtained.

Example 9

Solid OSCN⁻ Sodium Salt Obtained by Evaporation of the Solvents

A solution obtained according to example 1 ([OSCN⁻]=617 μmol·l−1) is diluted with absolute ethanol (EtOH/H2O of 9:1). The solvent is then evaporated in the form of an azeotrope at reduced pressure using a rotating evaporator (bath temperature of 40° C.) until the solvents are fully evaporated. The product obtained is a white powder. The OSCN⁻ content is checked by TNB colorimetric test (Ellman reagent). 20 μg of OSCN⁻ is obtained, this being a yield of 21%.

Example 10

Solid OSCN⁻ Sodium Salt Obtained by Evaporation of the Solvents

A solution obtained according to example 1 ([OSCN⁻]=1340 μmol·l−1) is diluted with absolute ethanol (EtOH/$H_2O$ of 9:1). The solvent is then evaporated in the form of an azeotrope at reduced pressure using a rotating evaporator (bath temperature of 40° C.) until the solvents are fully evaporated. The product obtained is a white powder. The OSCN⁻ content is checked by TNB colorimetric test (Ellman reagent). 100 μg of OSCN⁻ is obtained, this being a yield of 51%.

Example 11

RMN of an OSCN− Solution Reconstituted from a Solid Composition Containing Carbonate. (FIG. 2)

The hypothiocyanite has been generated by the glucose-oxidase/lactoperoxidase system according to example 1. ([OSCN−]=1240 umol·l−1). After ultra-filtration, $Na_2CO_3$ (1 mmol, 0.106 g) to 5 mL of filtrate is added. After complete dissolution, the solution is diluted with 95 mL of ethanol and evaporated at reduced pressure (30 mbar) at 30° C. One obtains a white powder that is solubilized in 0.6 mL of $D_2O$ and 20 μl of [2-$^{13}C$]-Gly used as external reference.

FIG. 2 shows the $^{13}C$ RMN spectrum of solid composition 1 containing OSCN⁻. The sample has been prepared with 0.1 g of solid filtrate composition, 0.5 mL of $D_2O$ and 20 μL of [2-$^{13}C$]-Gly (0.1 M). The NaS$^{13}$CN (Sigma-Aldrich) has been used as substrate. In both cases, the sample has been analyzed within 15 minutes following synthesis. The spectrum is calibrated for [2-$^{13}C$]-Gly used as external reference (the splitting in two of the signal in the carbonate buffer is due to the pH effect). The spectrums have been recorded for 3 hours on a Bruker AM-500WB type device with a spectral window of 25000 Hz. Chemical shifts: (a) 162.1 ppm=$CO_3^{2-}$ (b) 134.7 ppm=SCN⁻ (c) 129.8 ppm=OCN⁻ (d) 128.6 ppm=OSCN−; (e) Signals of glucose and gluconic acid (f) 42.7 and 47.5 ppm=[2-$^{13}C$]-glycine (the splitting in two of the signal in the carbonate buffer is due to the pH effect).

Example 12

RMN of an OSCN− Solution Reconstituted from a Solid Composition Containing the Lactose Excipient. (FIGS. 3A and 3B).

Hypothiocyanite has been generated by the glucose-oxidase/lactoperoxidase system according to example 1. ([OSCN−]=1540 μmol·l$^{−1}$). After ultra-filtration, $Na_2CO_3$ (1 mmol, 0.106 g) and lactose (0.5 mmol, 0.171 g) are added to 10 mL of filtrate. After complete dissolution, the solution is diluted with 190 mL of ethanol and evaporated at reduced pressure (40 mbar) at 25° C. One obtains a white powder that is solubilized in 0.6 mL of $D_2O$ and 20 μL of [2-$^{13}C$]-Gly used as external reference.

FIGS. 3A and 3B illustrate the $^{13}C$ RMN spectrum of solid composition 2 containing OSCN−. The sample has been prepared from 0.1 g of solid filtrate composition, 0.5 mL of $D_2O$ and 20 μl of [2-$^{13}C$]-Gly (0.1 M). NaS$^{13}$CN (Sigma-Aldrich) has been used as substrate. In both cases, the sample has been analyzed within 15 minutes after synthesis. The spectrum is calibrated for [2-$^{13}C$]-Gly used as external reference (the splitting in two of the signal in the carbonate buffer is due to the pH effect). The spectrums have been recorded for 3 hours by a Bruker AM-500WB type device with a spectral window of 25000 Hz. Chemical shifts: (a) 162.1 ppm=$CO_3^{2-}$ (b) 134.7 ppm=SCN⁻ (c) 129.8 ppm=OCN⁻ (d) 128.6 ppm=OSCN⁻; (e) Signals of lactose, glucose and gluconic acid (f) 42.7 and 47.5 ppm=[2-$^{13}C$]-glycine (the splitting in two of the signal in the carbonate buffer is due to the pH effect).

Example 13

Solid OSCN− Sodium Salt Obtained by Using $CO_2$ as Anti-Solvent

A solution obtained according to example 1 ([OSCN−]=1610 μmol·l−1) is diluted with absolute ethanol (EtOH/H2O of 9:1) containing 1 mmol of Lactose. The solvent is then introduced in the reaction cell at a pressure of 73 bar at 35° C. using a capillary; the solution is dispersed in the form of a jet in the super critical phase circulating at co-current. Precipitation permits to obtain a product in the form of a white powder in the precipitation cell after depressurizing.

Content in OSCN– is checked by TNB colorimetric test (Ellman reagent).

92 μg of OSCN– is obtained, this being a yield of 39%.

Example 14

Stability of Solid Composition No. 2 Containing Hypothiocyanite

To study the stability of the solid composition of this invention, stocks have been prepared. The hypothiocyanite has been generated in a solution by the lactoperoxidase system according to the procedure described previously. To 10 ml of filtrate, $Na_2CO_3$ (1 mmol; 0.106 g) and lactose (2 mmol; 0.7 g) are added. After complete dissolution, the solution has been diluted with ethanol (190 ml) and evaporated dry at reduced pressure (40 mbar) at 25° C. Three lots have been prepared according to the same procedure. The powders are collected and 0.1 g has been prepared in closed plastic flasks.

Figure 4:
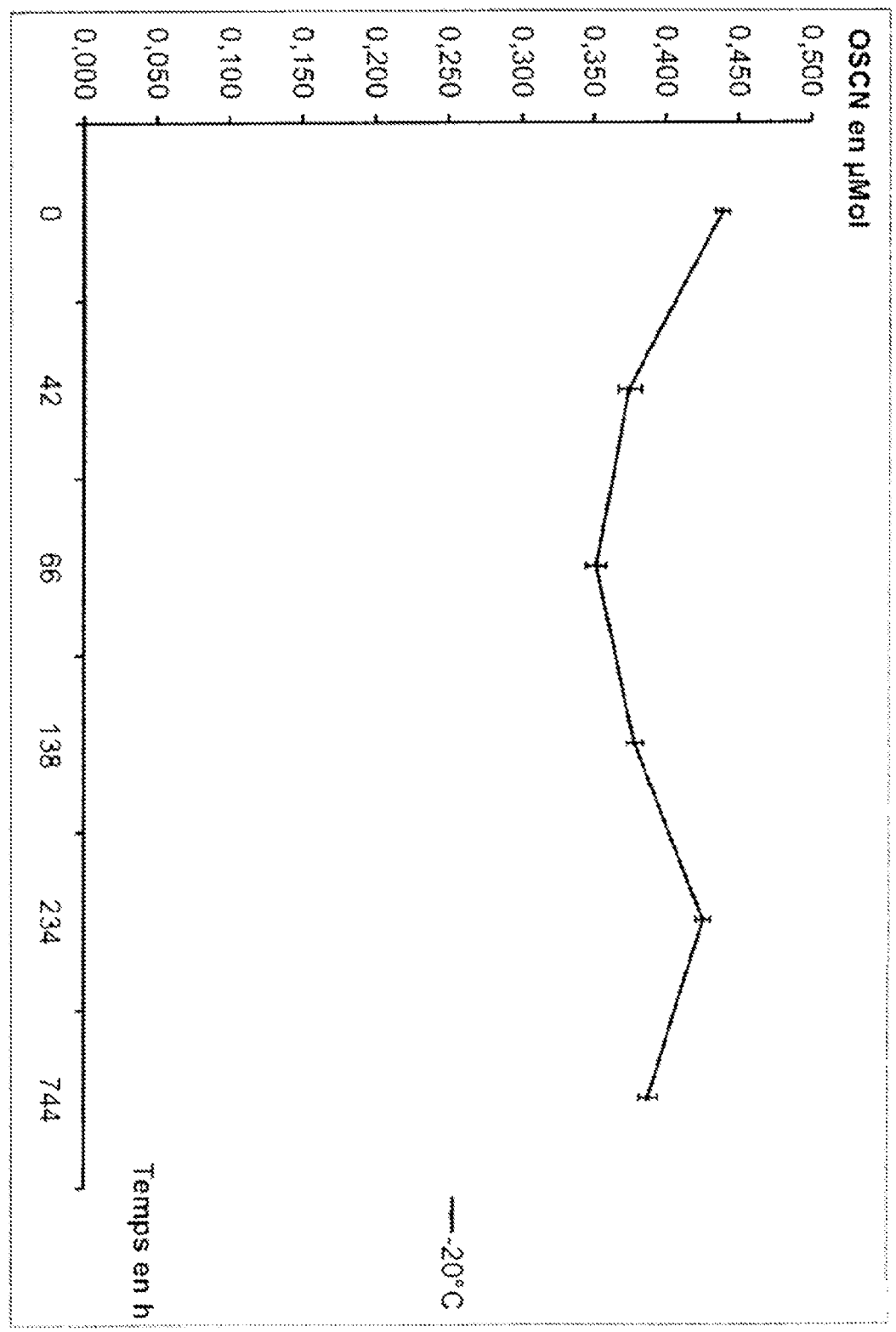
FIG. 4: Measurement of the stability of solid composition No. 2 containing hypothiocyanite.

The samples have been preserved at –18° C. and the quantity of $OSCN^-$ has been measured after preserving the solid composition for different time periods (0, 42, 66, 138, 234, 744 hours). The measurement of the hypothiocyanite volume by the TNB method has been done as follows: the concentration of $OSCN^-$ has been determined in the samples after dilution in 1 ml of pure water, by loss of absorption at 412 nm of a TNB solution as stated before. The measurements have been duplicated. The results show that the solid composition according to this invention is stable over time. Stability is practically identical to time zero at time 42 hours or 744 hours (Table 2, FIG. 4).

TABLE 2

OSCN-volume measured from 2 samples 1 and 2 of the solid composition of the invention after conservation at –20° C. for a variable period of time.

| Time (hrs) | Sample 1 | | Sample 2 | | OSCN μmol (average) | Relative loss | ET |
|---|---|---|---|---|---|---|---|
| | OSCN_Umol | ET | OSCN_Umol | ET | | | |
| 0 | 0.434 | 0.011 | 0.445 | 0.009 | 0.439 | | 0.010 |
| 42 | 0.381 | 0.015 | 0.370 | 0.016 | 0.375 | 14.58% | 0.016 |
| 66 | 0.350 | 0.014 | 0.354 | 0.014 | 0.352 | 19.85% | 0.014 |
| 138 | 0.380 | 0.010 | 0.378 | 0.012 | 0.379 | 13.74% | 0.011 |
| 234 | 0.433 | 0.011 | 0.320 | 0.010 | 0.426 | 2.96% | 0.011 |
| 744 | 0.410 | 0.013 | 0.368 | 0.013 | 0.389 | 11.53% | 0.013 |

The invention claimed is:

1. A solid composition comprising at least an $OSCN^-$ hypothiocyanite salt combined with a cation and an osidic, polyosidic, or polyol excipient, wherein the solid composition has the form of an amorphous and/or crystalline powder.

2. The solid composition according to claim 1, wherein the percentage by weight of the $OSCN^-$ hypothiocyanite salt combined with a cation in the composition falls between 0.01 and 20%.

3. The solid composition according to claim 1, wherein the solid composition further comprises an $SCN^-$ thiocyanate ion salt in a percentage by weight between 0.01% and 40%.

4. The solid composition according to claim 1, wherein the solid composition further comprises a gluconic acid in a percentage by weight between 0.01% and 20%.

5. The solid composition according to claim 1, wherein the solid composition further comprises a phosphate or carbonate salt (combined with an alkaline cation), in a percentage by weight between 10% and 99.999%.

6. The solid composition according to claim 1, wherein the cation is selected from the group consisting of sodium, potassium, calcium and magnesium.

7. The solid composition according to claim 1, wherein the solid composition comprises a combination of at least two of said osidic, polysidic and polyols excipients.

8. A manufacturing process of the solid composition according to claim 1, the process comprising:
   a) preparing an aqueous solution containing at least the $OSCN^-$ hypothiocyanite ion;
   b) adding to said aqueous solution, at least an alcohol or an organic solvent taken from among the azeotropes of water, at a percentage between 10 and 99.9%;
   c) adding an osidic, polyosidic or polyol excipient; and
   d) eliminating the alcohol or the organic solvent at a pressure between 1 mbar and 80 bars and a temperature between –100° C. and +50° C. in order to obtain the solid composition.

9. The manufacturing process according to claim 8, wherein the organic solvent is selected from the azeotropes of water and combinations thereof.

10. The manufacturing process according to claim 8, wherein the alcohol is ethanol, propanol, isopropanol, tert-butanol, or a mixture thereof.

11. The manufacturing process according to claim 8, wherein the excipient is a mixture of at least two of said osidic, polysidic, and polyol excipients.

12. The manufacturing process according to claim 8, wherein the temperature is between –100° C. and 0° C.

13. The manufacturing process according to claim 8, wherein step a) comprises preparing the aqueous solution containing the $OSCN^-$ hypothiocyanite ion by the placing in contact with a peroxidase, a pseudohalogen, and/or a halogen and an oxygen donor.

14. A method for treating an airborne infection, an infection of the lower respiratory tract and/or an infection of the upper respiratory tract in a subject in need thereof, the method comprising administering to the subject the solid composition of claim 1, alone or in combination with an anti-infectious, antimicrobial, antiviral, antibiotic, antifungal agent, or preservative.

15. The method according to claim 14, for treatment a pulmonary infection combined with cystic fibrosis and COPD (Chronic Obstructive pulmonary disease).

16. A method for treating a gastric infection, or an infection of cuts, mucous membranes and/or the skin in a subject in need thereof, the method comprising administering to the subject the solid composition of claim 1, alone or in combination with an anti-infectious, antimicrobial, antiviral, antibiotic, antifungal agents or preservatives.

17. A method for treating an infection caused by a bacteria, yeast, mold, virus, parasite, and/or protozoan in a subject in need thereof, the method comprising administering to the subject the solid composition of claim 1, alone or in combination with an anti-infectious, antimicrobial, antiviral, antibiotic, antifungal agent, or preservative 18. A method for treating an influenza virus infection in a subject in need thereof, the method comprising administering to the subject the solid composition of claim 1, alone or in combination with an anti-infectious, antimicrobial, antiviral, antibiotic, antifungal agent, or preservative.

19. A method for treating a microbial infection in a subject in need thereof, the method comprising administering to the subject the solid composition of claim 1, in combination with a protein or peptide having antimicrobial activity selected from the group consisting of lactoferrin, lactoferricin, and lysozyme.

* * * * *